(12) United States Patent
Yu et al.

(10) Patent No.: US 10,364,361 B2
(45) Date of Patent: Jul. 30, 2019

(54) WEATHERPROOF AQUEOUS WOOD COATINGS

(71) Applicant: Akzo Nobel Chemicals International B.V., Arnhem (NL)

(72) Inventors: Hua Yu, Scarsdale, NY (US); Lingjuan Shen, Yardley, PA (US)

(73) Assignee: AKZO NOBEL CHEMICALS INTERNATIONAL B.V., Arnhem (NL)

( * ) Notice: Subject to any disclaimer, the term of this patent is extended or adjusted under 35 U.S.C. 154(b) by 0 days.

(21) Appl. No.: 15/535,480

(22) PCT Filed: Dec. 11, 2015

(86) PCT No.: PCT/EP2015/079386
§ 371 (c)(1),
(2) Date: Jun. 13, 2017

(87) PCT Pub. No.: WO2016/096642
PCT Pub. Date: Jun. 23, 2016

(65) Prior Publication Data
US 2017/0349768 A1    Dec. 7, 2017

Related U.S. Application Data

(60) Provisional application No. 62/091,870, filed on Dec. 15, 2014.

(30) Foreign Application Priority Data

Jan. 22, 2015 (EP) ..................... 15152053

(51) Int. Cl.
| | |
|---|---|
| C09D 5/14 | (2006.01) |
| C08K 5/19 | (2006.01) |
| A01N 33/12 | (2006.01) |
| B27K 3/34 | (2006.01) |
| C09D 7/63 | (2018.01) |
| C09D 5/02 | (2006.01) |
| C09D 15/00 | (2006.01) |
| B27K 5/02 | (2006.01) |
| C09D 5/24 | (2006.01) |
| C08K 5/17 | (2006.01) |
| B27K 3/36 | (2006.01) |

(52) U.S. Cl.
CPC .................. *C09D 7/63* (2018.01); *B27K 5/02* (2013.01); *C08K 5/17* (2013.01); *C09D 5/02* (2013.01); *C09D 5/024* (2013.01); *C09D 5/24* (2013.01); *C09D 15/00* (2013.01); *A01N 33/12* (2013.01); *B27K 3/34* (2013.01); *B27K 3/36* (2013.01); *B27K 2240/70* (2013.01); *B27K 2240/90* (2013.01); *C08K 5/19* (2013.01); *C08L 2201/54* (2013.01); *C09D 5/14* (2013.01)

(58) Field of Classification Search
CPC ...... C09D 7/63; C09D 15/00; B27K 2240/70; B27K 3/34; B27K 3/36; A01N 33/12
See application file for complete search history.

(56) References Cited

U.S. PATENT DOCUMENTS

| | | | |
|---|---|---|---|
| 4,866,106 A | 9/1989 | Pellow et al. | |
| 5,089,342 A | 2/1992 | Dhein et al. | |
| 5,141,784 A | 8/1992 | Beane et al. | |
| 5,284,690 A | 2/1994 | Williams et al. | |
| 6,077,888 A | 6/2000 | Schilling | |

(Continued)

FOREIGN PATENT DOCUMENTS

| | | | | |
|---|---|---|---|---|
| BE | 1014749 A6 | 3/2004 | | |
| GB | 2438404 A | * | 11/2007 | ............. A01N 33/12 |
| JP | H02-70769 A | 3/1990 | | |
| JP | 2002-534539 A | 10/2002 | | |
| JP | 2004-502017 A | 1/2004 | | |
| JP | 2004-509983 A | 4/2004 | | |
| WO | 00/40627 A1 | 7/2000 | | |
| WO | 00/058028 A1 | 10/2000 | | |
| WO | 02/00799 A1 | 1/2002 | | |
| WO | 02/24756 A2 | 3/2002 | | |

OTHER PUBLICATIONS

European Search Report issued in EP Application No. 15152053.3 dated Mar. 17, 2015.

(Continued)

*Primary Examiner* — Ramsey Zacharia
(74) *Attorney, Agent, or Firm* — Matthew J. DeRuyter

(57) ABSTRACT

An aqueous based coating composition comprising a fatty amine quaternary having the structure of formula (I): $R^1R^2R^3R^4N^+X^-$ wherein $R^1$, $R^2$, $R^3$, and $R^4$ are independently selected from saturated or unsaturated, linear or branched, substituted or unsubstituted alkyl, aralkyl, or alkenyl groups comprising from 1 to 30 carbon atoms, whereby at least one of $R^1$, $R^2$, $R^3$, and $R^4$ is a C12-C30 group, and $X^-$ is an anion from an inorganic or organic acid, is provided. The fatty amine quaternary may contain ethoxy and/or propoxy groups. One or more of $R^1$, $R^2$, $R^3$, and $R^4$ may be substituted and contain one or more hydroxyl substituents or ether linkages. Methods for imparting water resistance to a wood substrate having up to 100% moisture by applying a coating composition having the fatty amine quaternary of formula (I), and for preparing an aqueous coating composition comprising the fatty amine quaternary of formula (I) are provided. Also provided is a coated water resistant wood substrate comprising the fatty amine quaternary of formula (I).

19 Claims, No Drawings

(56) References Cited

U.S. PATENT DOCUMENTS

| | | | |
|---|---|---|---|
| 6,464,764 B1 * | 10/2002 | Lichtenberg | C09D 191/005 106/15.05 |
| 6,734,266 B2 | 5/2004 | Gao et al. | |
| 7,071,260 B1 | 7/2006 | Kuropka et al. | |
| 7,691,482 B2 | 4/2010 | Zhu et al. | |

OTHER PUBLICATIONS

International Search Report and Written Opinion for PCT/EP2015/079386 dated Jan. 19, 2016.
International Preliminary Report on Patentability for PCT/EP2015/079386 dated Nov. 2, 2016.

* cited by examiner

WEATHERPROOF AQUEOUS WOOD COATINGS

This application is a national stage filing under 35 U.S.C. § 371 of PCT/EP2015/079386, filed Dec. 11, 2015, which claims priority to U.S. Provisional Patent Application No. 62/091,870, filed Dec. 15, 2014 and European Patent Application No. 15152053.3, filed Jan. 22, 2015, the contents of each of which are each incorporated herein by reference in their entirety.

FIELD OF THE INVENTION

The field relates to wood coating formulations, and methods of producing such coatings. More specifically, the field relates to aqueous coating formulations which can be applied by the user to wood substrates.

BACKGROUND

Wood stain formulations are applied to exterior wood surfaces such as wood furniture or fixtures to extend the life of the wood surface, maintain the appearance of the surface, and/or to improve the performance or durability of the wood substrate. Exterior wood surfaces are exposed to extreme weather conditions such as snow, heat, sun, and rain, causing wood to be susceptible to mold, mildew, and damage from UV exposure. Wood stain formulations providing one or more functions such as stain resistance, mold and mildew resistance, antimicrobial properties, and pest resistance are used to extend the durability of the wood substrate.

Wood stain formulations may be oil based or solvent based systems. Oil based systems can require lengthy drying times. Non-aqueous solvent based systems may have shorter drying times, but are less ecologically friendly due to the use of solvent. In view of environmental legislation that has established limits on the amounts of volatile organic compounds (VOCs) which are allowed in different coating systems, there has been a shift away from solvent borne coatings to water borne systems.

Water based coatings are more ecologically friendly. However, one disadvantage of waterborne coatings is that such coating compositions dry at a rate which depends on the temperature and humidity of the coating environment. Under low humidity conditions, waterborne coatings may dry rapidly. However, at higher atmospheric humidity, drying times are longer due to the slower evaporation of water from the coating composition. As such, certain water based coatings become water resistant only after extended drying times.

Wood stain formulations typically require the substrate to be dry before coating, which often means that the user must wait one to two days for the substrate to dry before applying the coating. Some wood stain formulations also prescribe that coatings may be applied only within certain temperature ranges, and only if rain is not expected for the next 24 hours or more.

Current aqueous coating compositions are disadvantageous because they require a sufficiently dry substrate, and/or rain free weather conditions post application, as well as drying times that are dependent on temperature and humidity conditions.

Accelerated drying of waterborne coating compositions which do not require the substrate to be dry prior to application, and can dry rapidly even under high atmospheric humidity is desirable.

Attempts have been made to improve drying times of aqueous coatings by incorporating a quaternary poly(allylamine) into the coating compositions as a drying accelerator. U.S. Pat. No. 7,071,260 relates to rapid-curing aqueous coating agents containing at least one binding agent and at least one water-soluble, quaternary poly(allylamine). However, such coating compositions are not suitable for weatherproof type of application and requires additional emulsifier to incorporate the quaternary poly(allylamine).

Other approaches to improving air drying times include the use of an air drying agent by reaction of epoxy containing polyacrylates, fatty acid, and monoamine ammonium salts. U.S. Pat. No. 5,089,342 relates to an aqueous coating agent for providing a decorative and protective coating for wood or wood products which contains as a binder, polyacrylate resins having chemically incorporated therein air-drying, unsaturated fatty acid moieties and quaternary ammonium moieties.

U.S. Pat. No. 5,284,690 describes an article comprising an aqueous release coating which includes a polymer and an aqueous solution or dispersion of an organic compound having at least one fatty acid ester and at least one quaternary amine.

BE1014749 relates to an additive for coating compositions comprising nonionic and/or cationic surfactant, alkali metal metasilicate, alkali metal gluconate, glycol, and water.

U.S. Pat. No. 6,077,888 relates to bituminous emulsions which can be used to produce bituminous emulsions exhibiting high viscosity and low asphalt residues. The emulsifying compositions are combinations of fatty amine and/or polyamine, lignin, and non-ionic surfactant.

Accordingly, there is a need for weatherproof coating systems which allow the user more flexibility in coating exterior substrates, such as by providing faster drying times without requiring the substrate to be dry prior to application, and without requiring the coated substrate to remain dry post application.

SUMMARY

An aqueous based coating composition comprising a fatty amine quaternary having the structure of formula (I):

$$R^1R^2R^3R^4N^+X^- \tag{I}$$

wherein $R^1$, $R^2$, $R^3$, and $R^4$ are independently selected from saturated or unsaturated, linear or branched, substituted or unsubstituted, alkyl, aralkyl, or alkenyl groups comprising from 1 to 30 carbon atoms, whereby at least one of $R^1$, $R^2$, $R^3$, and $R^4$ is a C4-C30 group, and $X^-$ is an anion from an inorganic or organic acid, is provided. The fatty amine quaternary may contain ethoxy and/or propoxy groups. One or more of $R^1$, $R^2$, $R^3$, and $R^4$ may be substituted and contain one or more hydroxyl substituents or ether linkages.

In another aspect, a method of imparting water resistant to a substrate having a moisture content up to 100% is provided. In one approach, the method includes applying an aqueous based coating composition comprising a fatty amine quaternary of formula (I) to a wooden substrate. A coated substrate comprising the fatty amine quaternary is also described.

A method of preparing an aqueous based coating composition comprising a fatty amine quaternary of formula (I) is also provided.

As discussed in more detail below, the aqueous based coating composition and methods of weatherproofing a wood substrate provides improved convenience for the consumer by providing faster drying times and allowing for application onto a substrate which is not fully dried. The seasons during which the user may apply a coating is extended as the user is less dependent on weather and other environmental conditions in order to successfully impart water resistance to the substrate.

DETAILED DESCRIPTION

This disclosure relates generally to aqueous coating compositions for imparting water resistance to substrates, and methods of imparting water resistance to substrates. Weatherproofing substrates, such as by imparting water resistance, provides the substrate with less susceptibility to weather and exposure related damage, and can extend and/or improve the performance of the substrate. A method of preparing an aqueous coating composition which provides early moisture resistance to a substrate, and a coated water resistant substrate are also provided.

The aqueous based coating composition of the present disclosure provides enhanced flexibility in application previously not achieved by prior weatherproof coating systems. The aqueous based coating composition of the present disclosure provides water resistance earlier in the coating process by not requiring the substrate to be dry prior to applying a coating to the substrate. Furthermore, early water resistance in the coating process is also achieved as the present coating formulation dries rapidly, does not need extended drying times required by other water based coating compositions.

The substrates of the present disclosure include a wide variety of substrates, made from various materials, such as wood, plastic, paper or cardboard. In some aspects the substrate is a porous substrate, such as a wood substrate.

In one approach, the invention relates to wood substrates. Examples of wood substrates include, but are not limited to: oak, maple, yellow pine, birch, spruce, walnut, poplar, and aspen. Other wood substrates may also be used, as well as various veneer substrates. Such wood substrates may be surfaces which are exposed to exterior environments, such as outdoor decks, furniture, or fixtures.

The aqueous coating composition of the present disclosure comprises a fatty amine quaternary of formula (I):

$$R^1R^2R^3R^4N^+X^- \qquad (I)$$

wherein $R^1$, $R^2$, $R^3$, and $R^4$ are independently selected from saturated or unsaturated, linear or branched, substituted or unsubstituted, alkyl, aralkyl, or alkenyl groups comprising from 1 to 30 carbon atoms, whereby at least one of $R^1$, $R^2$, $R^3$, and $R^4$ is a C4-C30 group, and $X^-$ is an anion from an inorganic or organic acid. Any of $R^1$, $R^2$, $R^3$, and $R^4$ may contain a hydroxyl substituent or ether linkage. The fatty amine quaternary of formula (I) may contain ethoxy and/or propoxy groups.

Any source can be used to provide the R groups of the quaternary ammonium compound of formula (I). Suitably one R group, two, three, or all four R groups is/are derived from a natural source. Suitably the C4-C30 group is derived from a natural source. Preferred natural sources are oils and fats, such as oils and fats from land animals, marine animals, and plants. Sources of fat and oils from land animals include butterfat, depot fat, lard oil, neat's foot oil, and tallow (such as from beef or mutton). Sources of fat and oils from marine animals include cold-liver oil, herring oil, menhaden oil, sardine oil, sperm oil, and whale oil. Sources of fats and oils from plants include babassu oil, castor oil, cocoa butter, coconut oil, corn oil, cotton seed oil, linseed oil, mustard oil, neem oil, niger-seed oil, oiticica oil, olive oil, palm oil, palm-kernel oil, peanut oil, perilla oil, poppy-seed oil, rapeseed oil, safflower oil, sesame oil, soybean oil, sunflower-seed oil, tall oil, tung oil, and wheat germ oil.

In one approach, suitable oils and fats are selected from the group consisting of coconut, soybean (soya), tallow, palm, palm kernel, rapeseed, lard, sunflower, corn, safflower, canola, olive, peanut, and combinations thereof. In another approach, the suitable oils and fats are selected from the group consisting of soybean oil, tallow or coconut oil, such as fully or partially hydrogenated soybean oil, fully or partially hydrogenated tallow, or fully or partially hydrogenated coconut oil. In some approaches, the fatty acid is fully or partially hydrogenated tallow, and in certain approaches, the source of the fatty acid is fully hydrogenated tallow.

Suitable fatty acids may include saturated acids such as isovaleric acid, valeric acid, caproic acid, enanthic acid, caprylic acid, pelargonic acid, capric acid, lauric acid, tridecylic acid, myristic acid, pentadecylic acid, palmitic acid, margaric acid, stearic acid, arachidic acid, phytanic acid, behenic acid, lignoceric acid, cerotic acid and montanic acid; or monounsaturated acids such as caproleic acid, palmitoleic acid, oleic acid, vaccenic acid, elaidic acid, brassidic acid, erucic acid, and nervonic acid; diunsaturated acids such as linoleic acid; triunsaturated acids such as eleosteric acid and linolenic acid; and tetraunsaturated acids such as arachidonic acid. In some approaches, the fatty acids are stearic acid, arachidic acid, phytanic acid, behenic acid, lignoceric acid, cerotic acid, montanic acid, oleic acid, vaccenic acid elaidic acid, brassidic acid, erucic acid, nervonic acid, linoleic acid, eleosteric acid, linolenic acid, and arachidonic acid. In yet other approaches, the suitable fatty acids are selected from the group consisting of stearic acid, oleic vaccenic acid, elaidic acid, linoleic acid, eleosteric acid, linolenic acid.

One or more, such as two or more, three or more, or all four of $R^1$, $R^2$, $R^3$, and $R^4$ is/are a linear or branched alkyl or alkenyl radical(s) comprising C1-C30, such as C4-C30, or C18-C30. In some approaches, one or more, such as two or more, three or more, or all four of $R^1$, $R^2$, $R^3$, and $R^4$ comprise at least C6, at least C8, such as at least C12, or C12-C18. In other approaches, one or more, such as two or more, three or more, or all four of $R^1$, $R^2$, $R^3$, and $R^4$ comprises C18-C30. In one aspect, at least one, at least two, at least three, or all four of $R^1$, $R^2$, $R^3$, and $R^4$ is/are a C18 linear or branched alkyl or alkenyl radical. In one approach, one or more of $R^1$, $R^2$, $R^3$, and $R^4$ may be an aralkyl group. Such aralkyl group may be derived from non-natural resources, such as a resin or a rosin.

One or more of $R^1$, $R^2$, $R^3$, and $R^4$ may be saturated or unsaturated. The $R^1$, $R^2$, $R^3$, and $R^4$ groups each may have an iodine value of 5-30. One or more of $R^1$, $R^2$, $R^3$, and $R^4$ may be hydrogenated, such as partially or fully hydrogenated. In some approaches, one or more, such as two or more, three or more, or all four of $R^1$, $R^2$, $R^3$, and $R^4$ may be fully hydrogenated. In yet other approaches, one or more, such as two or more, three or more, or all four of $R^1$, $R^2$, $R^3$, and $R^4$ may be fully or partially hydrogenated linear or branched alkyl or alkenyl radicals comprising C18, such as fully hydrogenated radicals comprising C18, such as fully hydrogenated C18 radials derived from oleic acid.

In formula (I), $X^-$ is the anion from an inorganic or organic acid such as $Cl^-$, $CH_3SO_4^-$, $Br^-$, and $CH_3CO_3^-$.

The fatty amine quaternary of formula (I) may comprise fatty acids which are ethoxylated, propxylated and/or butoxylated. In some approaches the fatty amine quaternary comprises about 1 to about 30 alkoxy units, or about 1 to about 20 alkoxy units, such as about 1 to about 15 alkoxy units, or about 1 to about 10 alkoxy units. In one aspect such alkoxy groups are ethoxy groups. In other aspects, the fatty amine quaternary comprises from about 1 to about 10 propoxy units, such as from about 1 to about 5 propoxy units. In one approach, the number of ethoxy and propoxy groups, is between 1 and 40, such as between 2 and 20. The fatty amine quaternary structure may be ethoxylated and/or propoxylated in any order, either randomly or blocky. In one approach, the fatty amine quaternary is a blocked alkoxylated fatty amine quaternary.

The fatty amine quaternary may be propoxylated prior to ethoxylation. In some approaches, the ethoxylation to propoxylation ratio is from 2:1 to 6:1, such as 3:1 to 6:1, 4:1 to 6:1, 5:1 to 6:1, 3;1 to 5:1, or 4:1 to 6:1.

Without wishing to be bound by any particular theory, it is believed that the head group of the ethoxylated fatty amine quaternary has affinity for wood, which is negatively charged when wet, and thus is oriented such that the fatty tails are oriented towards the air surface of the coating to convey water resistant properties. The incorporation of a fatty amine quaternary to existing wood stain formulations such as Dulux® Trade Weathershield Aquatech, from AkzoNobel Inc. may be further stabilized by ethoxylation of the fatty amine quaternary, so that the orientation of one or more of the $R^1$, $R^2$, $R^3$, and $R^4$ chains are maintained.

When the orientation is maintained such that the fatty tails are oriented towards the air surface of the coating to convey water resistance properties, the aqueous coating composition provides a protective layer over the underlying wood substrate, even if the underlying wood substrate is not dry. The weatherproof aqueous coatings of the present disclosure can be applied to substrates that not dry, to provide weatherproof protection once applied to the wood substrate. The coatings of the present disclosure provides a quick drying-layer, but also provides protection during the drying process as the coatings of the present disclosure does not require any reactions, such as cross-linking, to occur before a protective layer is formed.

The fatty amine quaternary may be incorporated into existing wood stain formulations without the need for emulsifiers, such as nonionic surfactants, such as alkyl and/or aryl ethoxylates. In some approaches, the aqueous composition is substantially free of emulsifiers.

The fatty amine quaternary in the aqueous composition is composed of one quaternary functional group per molecule, and as such, has a higher reactivity as compared to a polyquaternary comprising more than one quaternary functional group per molecule. The number average of the molecular weight of the fatty amine quaternary is between about 100 g/mol to about 1500 g/mol, such as between about 150 g/mol to about 750 g/mol, or between about 200 g/mol to about 500 g/mol.

In some approaches, the aqueous coating composition comprises from about 0.1% to about 20%, such as about 0.1% to about 10%, such as about 1% to about 8%, such as about 3% to about 6%, by weight of a fatty amine quaternary, or between about 0.5% to about 5%, such as about 1% to about 3%, or about 1% to about 2% by weight. The coating composition may comprise a combination of one or more fatty amine quaternaries as part of a surfactant composition.

Other components of the aqueous coating composition include binders and additives. In one approach the binder comprises a latex, alkyd emulsion, or a hybrid system comprising a combination thereof. The latex may include acrylics such as vinyl acrylic, acrylic latex, or styrene acrylic; or polyurethane or epoxy. The alkyds are polyesters derived from alcohol and organic acids, such as a fatty acid modified polyesters which dry by auto-oxidation and therefore form a cross-linked network. In hybrid systems, the amount of latex, such as acrylic, in the hybrid composition may be from about 60% to about 90%, such as about 80%, and the alkyd level may range from about 10% to about 30%, such as about 20%. In some approaches, the amount of latex in the aqueous coating composition may be between about 40% to about 90% (% solids), such as between about 50% to about 90% (% solids), such as between about 60% to about 80%(% solids), or about 50% to about 80% (% solids). In other approaches, the amount alkyd in the aqueous coating composition may be between about 10% to about 90% (% solids), such as about 20% to about 80% (% solids), or about 10% to about 50% (% solids).

The coating composition of the present invention may optionally comprise up to 0.01 wt. % to 10 wt. % of additives, such as 1% to 8%, such as 3% to 6%, by weight additives. Without limitation, suitable additives include: surfactants, anti-oxidants, fillers, extenders, pigments, optical brighteners, light stabilizers, biocides, thickeners, preservatives, and, co-solvents. Any such additives present should be dispersed, preferably homogenously, throughout the coating composition.

Surfactants (surface-active agents) form an important group of additives which may be present in the coating composition to provide smooth, uniform coatings. Suitable surfactants include, but are not limited to, flow control agents, wetting agents, dispersants, adhesion enhancers and defoamers. The preferred surfactants are either non-ionic or anionic.

Flow control agents are organic compounds capable of helping the coating wet the substrate and flow over possible contaminations. Exemplary flow control agents are sold under the trade names BYK 344 (BYK Chemie, Wallingford, Conn.), Air Products HS-30, and Witco L-7500.

Exemplary pigments include titanium dioxide white, carbon black, lampblack, black iron oxide, red iron oxide, transparent red oxide, yellow iron oxide, transparent yellow oxide, brown iron oxide (a blend of red and yellow oxide with black), phthalocyanine green, phthalocyanine blue, organic reds (such as naphthol red, quinacridone red and toulidine red), quinacridone magenta, quinacridone violet, DNA orange, or organic yellows (such as monoazo yellow) and mixtures thereof. Particularly suitable pigments for inclusion in the coating composition are transparent iron oxide. Five colors of transparent iron oxide (yellow S102, red S202, black S301, brown S401 and green S501) are commercially available from Suncom, China.

The solids content of the aqueous coating composition may be from about 1% to about 60%, such as about 10% to about 50%, or about 20% to about 40% by weight of the aqueous coating composition. The viscosity of the aqueous coating composition may be from about 1 to about 100 Pa·s, such as about 10 to about 90 Pa·s, such as about 30 to about 70 Pa·s, or about 40 to about 60 Pa·s as measured using a Brookfield viscometer at 25° C. As would be recognized by a skilled practitioner, the viscosities which are appropriate for different application methods vary considerably. In one approach, the aqueous coating composition comprises about 20% to about 50% by weight of binder, about 2% to about 10% by weight of compatibilizer or solvent, such as toluene, about 0.5% to about 5% by weight of surfactant additive, less than about 5% of filler, pigment, and other additives, and about 50% to about 75% by weight water.

In some approaches, the aqueous coating composition is substantially free of polyethyleneimine. Substantially free as used herein means that the component is present at about 0.05 percent or less, and in some approaches, about 0.03 percent or less, such as 0.01 percent, or not present at all.

In other approaches, the aqueous coating composition is substantially free of short chain fatty acids, such as fatty acids which have chain lengths up to 8 carbons, such as between 1 to 4 carbons.

In one approach, the aqueous coating composition is substantially free of solvents such as ethylene glycol, diethylene glycol, butyl diglycol, and butoxy triglycol.

Turning now to the method of imparting water resistance to a substrate, the present disclosure provides a method of imparting water resistance to a substrate by applying to a substrate an aqueous coating composition comprising an aqueous solvent and a fatty amine quaternary of the structure (I) as presented above.

By one approach, the substrate is a wooden substrate. The wooden substrate to be coated may be of any form known in the art, including for example unedged timber, flitches, boules, half-edged boards, square-edged lumber, strips, squares, carcassing, truss beams, scantlings and tongue-and-groove flooring, such as parquet, decking (E2E or E4E), and anti-slip decking (1 or 2 sides). The coatings of the present invention may be applied to fully cover said substrates or to cover only parts thereof, including edges, curvilinear surfaces, routered and beveled areas. The particular wood surface to be coated may be cleaned and prepared for application of the disclosed coating compositions using methods, such as sanding, that will be familiar to those skilled in the art.

Surprisingly, contrary to prior aqueous coating compositions which require a fully dried substrate prior to application of weatherproof coating, the weatherproof aqueous coating compositions of the present disclosure do not require a fully dried substrate prior to application of the aqueous coating composition. The aqueous coating formulation can be applied to a substrate with a wide range of moisture contents, including application to a substrate which has been soaked in water for days. Furthermore, once applied, the weatherproof aqueous coating compositions do not require that the coated substrate be fully dried before improved water resistance is imparted. Early moisture or water resistance is achieved after drying for 30 minutes or less at 10° C., and at relative humidity of up to 85%.

The substrate may have a moisture content of up to 100%, such as between about 10% and about 80%, and such as between about 30% and about 50%. In some approaches, when the aqueous coating composition is applied to a substrate having about 30% to about 50% moisture, at least about 70% water resistance (relative to the water resistance achieved when the application is on a dried substrate, under the same drying conditions) is achieved.

The aqueous coating composition may applied by conventional application methods such as flooding, dipping, brushing, roll coating, doctor-blade application, printing methods, air-atomized spray, air-assisted spray, airless spray, high volume low pressure spray, air-assisted airless spray and high-speed rotation bell.

The coating may be applied in an amount of between about 0.1 grams to about 10 grams per 100 $cm^2$ (unit of surface area), such as between about 0.1 grams to about 5 grams, or about 0.3 grams to about 3 grams.

Turning now to the method of preparing the coating composition, the present disclosure provides a weatherproof aqueous coating composition prepared by incorporating a fatty amine quaternary of formula (I) into an aqueous wood stain coating composition. One or more of a fatty amine quaternary of formula (I) may be combined with a weatherproof aqueous coating composition to provide the weatherproof aqueous coating composition of the present disclosure.

The fatty amine quaternary of formula (I) may be incorporated by combining, such as by mixing, the quaternary additive and one or more components of a wood stain coating composition with a mixer. In one approach, the mixing may be achieved by operating a mixer at 300 RPM for at least 15 minutes at room temperature. Upon addition of the fatty amine quaternary additive to the wood stain formulation, the interactions between the quaternary additive and the components of the polymer system of the wood stain formulation may take a day, or several days, such as up to six days, to stabilize.

The coating composition comprising the fatty amine quaternary has a stable shelf life comparable to existing wood stain formulations. Even when exposed to elevated storage temperatures of 40° C., and for extended time periods such as up to 30 days, the coating composition of the present disclosure maintains suitable rheological properties.

A coated water resistant wood substrate comprising a fatty amine quaternary of formula (I) may be prepared by applying the aqueous coating composition to a substrate as described by the methods above.

A better understanding of the present embodiments and its many advantages may be clarified with the following examples. The following examples are illustrative and not limited thereof in either scope or spirit. Those skilled in the art will readily understand that variations of these components, methods, steps, and devices described in these examples can be used. Unless noted otherwise, all percentages and parts noted in this disclosure are by weight.

EXAMPLES

Example 1

This Example compares the performance of wood stain formulations comprising various quaternary additives stored under different conditions, against a control wood stain formulation without the quaternary additives, after the wood stain formulations are applied to a wet substrate and subjected to a water spray test.

Wood stain formulations were prepared as described in Table 1 by adding 1% fatty amine quaternary based on weight, to a control wood stain (Dulux Trade Weathershield Aquatech, from AkzoNobel Inc.). Formulations were prepared by mixing the quaternary additive and wood stain formulation with a mixer @ 300 rpm for at least 15 minutes at room temperature. Samples were then stored at 40° C. for 24 hours or for 6 days prior to application on wet pine wood panels.

Wet pine wood panels 30 cm×5 cm×1 cm in size were prepared by soaking the pine wood panels overnight in water. Prior to application of the wood stain formulations, the pine wood panels are removed from the water and wiped gently to remove any surface water. Wood stain formulations with and without the quaternary additives were applied to the surface of the pine wood panel using a standard paintbrush. Pine wood panels were selected because pine wood can reach higher wood moisture contents than most other wood types, thus allowing the pine wood panels to provide harsher, more challenging test conditions.

The amount of wood stain formulation applied onto each wood panel is weighed, and is determined to be about 2 grams on a 200 grams wood substrate. The coated panels are then left in a controlled environment with a temperature of about 10° C. and a relative humidity of 85% for 45 min prior to testing with a water spray test.

Portions of each panel are then subjected to a continuous pressure of water spray for 2 minutes to evaluate the panels' resistance to simulated rain. During the 2 minutes of continuous water spray, the panels are each exposed to about 510 mL of water. Panels are then left overnight at about 25° C. and about 40% RH to dry before being visually assessed.

TABLE 1

Quaternary additive used in the weatherproof wood stain coatings

| Sample No. | Quaternary Additive |
| --- | --- |
| Sample #1 | Alkoxylated mono tallow quaternary with 8 EO and 2 PO |
| Sample #2 | Ethoxylated mono tallow quaternary with 5 EO |
| Sample #3 | Ethoxylated mono tallow quaternary with 10 EO |
| Sample #4 | Ethoxylated mono tallow quaternary with 15 EO |
| Sample #5 | Ethoxylated mono tallow quaternary with 20 EO |
| Sample #6 | Ethoxylated mono tallow quaternary with 25 EO |
| Sample #7 | Ethoxylated mono tallow quaternary with 30 EO |

All the Samples #1-7, subjected to 1 or 6 days of storage at 40° C., show improved color retention and/or color uniformity over the control samples, indicating Samples #1-7's improved water resistance even when applied on to a wet wood substrate. At least Samples #1, #3, and #4 show good color retention and uniformity.

Example 2

This Example compares the amount of control and inventive coating that were removed or damaged from the wet pine wood by the water spray test using spectrophotometric analysis and by weighing the test panels.

(A) Color Measurement Using Spectrophotometer Analysis

Wet pine wood panels were prepared as described in Example 1. Control and inventive wood stain formulations Sample #1 and Sample #4 from 6 days of storage at 40° C. were applied to the wet pine wood panels as described in Example 1. The samples were allowed to dry at a temperature of 10° C. and a relative humidity of 85% for 5 minutes, 15 minutes, 25 minutes, 35 minutes, and 45 minutes prior to subjecting the pine wood panels to the water spray test of Example 1.

After water sprayed samples are dried, the color and image of the panels were measured by "Konica Minolata spectrophotometer (model# CM-2600D)" and "J Image Analysis Software" to evaluate the level of the coatings that were removed or damaged by water spray. The three coordinates of the Commission Internationale de l'Eclairage (International Commission on Illumination) (CIE) lab, L*, a* and b*, represent the lightness of the color.

Color measurement results of wood stain treated pine wood with various drying times after water spray test are shown in Table 2 below.

TABLE 2

| Drying Time @10° C., 85% RH | Sample | L*(D65)† | a*(D65)† | b*(D65)† |
| --- | --- | --- | --- | --- |
| 5 min | Pine wood w/o wood stain | 78.73 | 6.25 | 22.34 |
| | w/o quaternary | 71.71 | 9.25 | 31.85 |
| | w/Sample #1 | 61.97 | 14.36 | 37.76 |
| | w/Sample #4 | 60.9 | 14.39 | 36.88 |
| 15 min | Pine wood w/o wood stain | 80.69 | 5.77 | 23.12 |
| | w/o quaternary | 67.69 | 11.18 | 32.4 |
| | w/Sample #1 | 59.6 | 15.05 | 36.88 |
| | w/Sample #4 | 58.13 | 15.15 | 35.62 |
| 25 min | Pine wood w/o wood stain | 78.91 | 7.01 | 24.45 |
| | w/o quaternary | 67.03 | 11.53 | 32.99 |
| | w/Sample #1 | 57.35 | 16.14 | 37.73 |
| | w/Sample #4 | 61.46 | 14.12 | 36.81 |
| 35 min | Pine wood w/o wood stain | 81.81 | 5.73 | 22.46 |
| | w/o quaternary | 72.96 | 8.58 | 28.47 |
| | w/Sample #1 | 58.95 | 15.58 | 37.95 |
| | w/Sample #4 | 60.4 | 14.67 | 36.62 |
| 45 min | Pine wood w/o wood stain | 79.73 | 6.23 | 24.69 |
| | w/o quaternary | 70.1 | 9.98 | 30.94 |
| | w/Sample #1 | 65.08 | 12.94 | 35.39 |
| | w/Sample #4 | 68.74 | 11.29 | 33.12 |

†L* denotes the lightness of color, a* denotes the red/green value and b* denotes yellow/blue value. Higher values indicate a lighter color.

Results indicate that even with short drying times (5 min), Samples 1 and 4 show improved results over control wood stain formulations without a quaternary additive. At each of the drying times, Samples #1 and #4 provide improved L*(D65) over the control samples.

(B) Measurement of Wood Stain Residue by Weight

Wet pine wood samples coated with control and inventive Sample #1, Sample #4, and Sample #7 wood stain formulations of Table 1 were dried at 10° C. and 85% relative humidity for 45 minutes and subjected to the water spray test in accordance with Example 1.

The weight of the pine wood panel before and after the water spray test was recorded to determine the amount of coating lost to water spray. Measurement results comparing the amount of coating before and after the water spray test are show in Table 3 below.

TABLE 3

Measurement of wood stain residue by weight on wet pine wood after water spray test

| Sample | Water Spray Test (conditioned @10° C. 85 RH 45 min) | Dry Wood Weight (g) | Paint Weight (g) | Dry Painted Wood Weight (g) | Paint Residue weight (g) | Paint Residue Percentage |
| --- | --- | --- | --- | --- | --- | --- |
| w/o quaternary | Yes | 51.69 | 0.57 | 51.77 | 0.08 | 14.0% |
| w/ Sample #1 | Yes | 50.67 | 0.58 | 51.16 | 0.49 | 84.5% |
| w/ Sample #4 | Yes | 51.62 | 0.58 | 52.05 | 0.43 | 74.1% |
| w/ Sample #7 | Yes | 51.52 | 0.57 | 51.95 | 0.43 | 74.1% |

Results in Table 3 indicate that inventive wood stain formulations containing the quaternary additive retain a higher percentage of the coating after a water spray test than the control sample.

Example 3

Example 3 compares spectrophotometer color measurement data of wood stain treated pine wood panels after water spray tests for pine wood treated with wood stain formulations having varying amounts of ethoxylated mono tallow quaternary with 15 EO (Sample #4 of Table 1).

After water sprayed samples are dried, the color and image of the panels were measured by "Konica Minolata spectrophotometer (model# CM-2600D)" and "J Image Analysis Software" to evaluate the level of the coatings that were removed or damaged by water spray. L*, a* and b* are the three coordinates of CIELAB, with L*, denoting the lightness of the color, a* denoting the red/green value and b* denoting the yellow/blue value. ΔE is the color difference between treated and untreated wood. Lower ΔE indicates a lighter color.

Results are shown in Table 4 below.

TABLE 4

Spectrophotometer Color measurement on Dulux wood stain treated pine wood after water spray test by

| Sample | L*(D65) | a*(D65) | b*(D65) | ΔE |
|---|---|---|---|---|
| Pine wood w/o wood stain | 80.56 | 5.38 | 22.93 | |
| w/wood stain and 0% Sample #4 | 59.86 | 13.71 | 35.74 | 25.73 |
| w/wood stain and 0.5% Sample #4 | 59.38 | 13.59 | 35.12 | 25.78 |
| w/wood stain and 1% Sample #4 | 50.53 | 16.01 | 32.91 | 33.38 |
| Wood stain with 1.5% Sample #4 | 50.78 | 17.65 | 34.3 | 34.16 |
| w/wood stain and 2% Sample #4 | 53.41 | 16.61 | 35.45 | 30.81 |
| w/wood stain and 3% Sample #4 | 60.53 | 14.04 | 36.32 | 24.59 |
| w/wood stain and 5% Sample #4 | 62.69 | 13.06 | 35.69 | 22.28 |

Results from Table 4 indicate that the largest difference ΔE in treated and untreated wood is achieved when using between about 1% to about 2% of ethoxylated mono tallow quaternary with 15 EO, indicating that amounts of about 1% to about 2% of the quaternary additive provide better color (coating) retention.

Example 4

This Example compares the rheology of Control formulations and inventive formulations comprising Samples #1 and #4 after storage at 40° C.

The Control original Weathershield wood stain formulation is generally stable during storage at 40° C. for over a month with no significant formulation rheology change.

Beyond day 1, inventive formulations comprising quaternary additive Samples #1 and #4 respectively are generally stable during storage at 40° C., and have rheology profiles generally comparable to the Control formulation, indicating that the addition of quaternary additives Sample #1 and Sample #4 has minimal impact on the overall rheology of the wood stain formulations, and can maintain a stability comparable to the Control wood stain formulation.

Upon addition of quaternary additives to the wood stain formulation, the interactions between the quaternary additive and the remaining components of the wood stain formulation takes several days to complete and stabilize, which is illustrated by a comparison between the day 1 rheology profile and the day 6 (and beyond) rheology profile of inventive wood stain formulations containing quaternary additives Samples #1 and #4. Beyond day 1, such as at day 6 when the interactions between the quaternary additives and the components of the polymer system of the wood stain formulation have stabilized, the rheology of the Control and inventive formulations are comparable.

It will be understood that various changes in the details, materials, and arrangements of formulations and ingredients, which have been herein described and illustrated in order to explain the nature of the method and compositions, may be made by those skilled in the art within the principle and scope of the description and claims herein.

The invention claimed is:

1. An aqueous coating composition comprising:
an aqueous solvent,
a fatty amine quaternary having the following structure:

wherein $R^1$, $R^2$, $R^3$, and $R^4$ are independently chosen from saturated or unsaturated, linear or branched, substituted or unsubstituted, alkyl, aralkyl, or alkenyl groups, comprising from 1 to 30 carbon atoms, wherein at least one of $R^1$, $R^2$, $R^3$, and $R^4$ includes both a C12-C30 group and ethoxy and/or propoxy groups, wherein $X^-$ is an anion from an inorganic or organic acid, and wherein the number average molecular weight of the fatty amine quaternary is between about 100 g/mol and about 1500 g/mol, and
binder in an amount of between 40% to 90% by weight of the aqueous coating composition.

2. The aqueous coating composition of claim 1, wherein at least one of $R^1$, $R^2$, $R^3$, and $R^4$ contains a hydroxyl substituent or ether linkage.

3. The aqueous coating composition of claim 1, wherein the number of ethoxy groups is between 1 and 30.

4. The aqueous coating composition of claim 1, wherein the number of propoxy groups is between 1 and 10.

5. The aqueous coating composition of claim 1, wherein the number of ethoxy and propoxy groups is between 1 and 40.

6. The aqueous coating composition of claim 5, wherein the ethoxy and/or propoxy groups are in random or block configuration.

7. The aqueous coating composition of claim 1, wherein the fatty amine quaternary comprises a fatty acid component selected from the group consisting of tallow, coconut, soya, palm, palm kernel, tall oil, rapeseed, lard, sunflower oil, corn oil, safflower oil, canola oil, olive oil, and peanut oil.

8. The aqueous coating composition of claim 1, wherein the fatty amine quaternary comprises a fatty acid that is oleic acid or erucic acid.

9. The aqueous coating composition of claim 1, wherein at least two of $R^1$, $R^2$, $R^3$, and $R^4$ comprise at least six carbon atoms.

10. The aqueous coating composition of claim 1, wherein the fatty amine quaternary is present in an amount of from about 0.1 wt % to about 20 wt % of the aqueous coating composition.

11. A method of imparting water resistance to a wood substrate, the method comprising applying from 0.1 grams to 10 grams of the aqueous coating composition of claim 1 per 100 cm² of substrate surface area.

12. The method of claim 11, wherein the wood substrate has a moisture content between about 30% and about 50%, and wherein applying the aqueous coating to the wood substrate provides at least 70% water resistance to the wood substrate.

13. The method of claim 11, wherein the wood substrate has a moisture content between about 10% and about 80%.

14. A method of preparing an aqueous coating composition with early moisture resistance, comprising the step of:
combining the fatty amine quaternary of claim 1 with an aqueous coating composition containing a binder, such that the aqueous coating composition with early moisture resistance comprises the binder in an amount of between 40% to 90% by weight.

15. The aqueous coating composition of claim 1, wherein at least two of $R^1$, $R^2$, $R^3$, and $R^4$ comprise at least twelve carbon atoms.

16. The aqueous coating composition of claim 1, wherein at least three of $R^1$, $R^2$, $R^3$, and $R^4$ comprise at least twelve carbon atoms.

17. The aqueous coating composition of claim 1, wherein at least two of $R^1$, $R^2$, $R^3$, and $R^4$ comprise at least eighteen carbon atoms.

18. The aqueous coating composition of claim 1, wherein at least three of $R^1$, $R^2$, $R^3$, and $R^4$ comprise at least eighteen carbon atoms.

19. The aqueous coating composition of claim 1, wherein a ratio of ethoxy groups to propoxy groups is between 2:1 and 6:1.

* * * * *